United States Patent
Piron et al.

(10) Patent No.: US 9,770,209 B2
(45) Date of Patent: *Sep. 26, 2017

(54) OPEN ARCHITECTURE TABLETOP PATIENT SUPPORT AND COIL SYSTEM

(71) Applicant: INVIVO CORPORATION, Andover, MA (US)

(72) Inventors: Cameron Anthony Piron, Toronto (CA); Han Wang, Toronto (CA); Joshua Richmond, Toronto (CA); Jakub Jankowski, Toronto (CA); Christopher Luginbuhl, Toronto (CA)

(73) Assignee: INVIVO CORPORATION, Andover, MA (US)

( * ) Notice: Subject to any disclaimer, the term of this patent is extended or adjusted under 35 U.S.C. 154(b) by 387 days.

This patent is subject to a terminal disclaimer.

(21) Appl. No.: 14/293,411

(22) Filed: Jun. 2, 2014

(65) Prior Publication Data

US 2015/0141802 A1    May 21, 2015

Related U.S. Application Data

(63) Continuation of application No. 13/653,062, filed on Oct. 16, 2012, now Pat. No. 8,744,550, which is a
(Continued)

(51) Int. Cl.
| | |
|---|---|
| *A61B 5/05* | (2006.01) |
| *A61B 5/00* | (2006.01) |
| *G01R 33/36* | (2006.01) |
| *A61B 5/055* | (2006.01) |
| *G01R 33/341* | (2006.01) |
| *G01R 33/54* | (2006.01) |

(52) U.S. Cl.
CPC .......... *A61B 5/708* (2013.01); *A61B 5/0555* (2013.01); *G01R 33/36* (2013.01); *G01R 33/341* (2013.01); *G01R 33/546* (2013.01)

(58) Field of Classification Search
CPC ...... A61B 5/708; A61B 5/0555; G01R 33/36; G01R 33/341; G01R 33/546
USPC ...... 600/407–430; 324/318–322; 5/600, 601, 5/615
See application file for complete search history.

(56) References Cited

U.S. PATENT DOCUMENTS

| | | | | |
|---|---|---|---|---|
| 5,590,655 A | * | 1/1997 | Hussman | A61B 17/3403 600/414 |
| 6,675,037 B1 | * | 1/2004 | Tsekos | A61B 5/0555 600/417 |

(Continued)

*Primary Examiner* — Sanjay Cattungal

(57) ABSTRACT

An assembly for magnetic resonance imaging (MRI) of a patient and a method of magnetic resonance imaging (MRI) of a patient using different MRI scanners is disclosed. In one example, the assembly includes a plurality of RF coils, wherein the RF coils are configured to be positioned adjacent to an anatomy of interest, a patient support structure configured to support of the patient, a base removably coupled to the patient support structure, the base and the patient support being configured for receipt in the bore of an MRI scanner, and an interface coupled to the plurality of RF coils and to the MRI scanner and configured to connect the plurality of RF coils and the MRI scanner and to selectively control a first RF coil and a second RF coil included in the plurality of RF coils.

20 Claims, 5 Drawing Sheets

Related U.S. Application Data continuation of application No. 12/277,061, filed on Nov. 24, 2008, now Pat. No. 8,290,569.

(60) Provisional application No. 60/989,898, filed on Nov. 23, 2007, provisional application No. 60/989,904, filed on Nov. 23, 2007.

(56) References Cited

U.S. PATENT DOCUMENTS

| | | | | |
|---|---|---|---|---|
| 6,822,450 B2* | 11/2004 | Klinge | G01R 33/5611 | 324/318 |
| 6,904,305 B2* | 6/2005 | Tsekos | A61B 5/0555 | 600/417 |
| 7,379,769 B2* | 5/2008 | Piron | A61B 8/0825 | 5/601 |
| 7,937,132 B2* | 5/2011 | Piron | A61B 8/0825 | 5/600 |
| 7,970,452 B2* | 6/2011 | Piron | A61B 5/415 | 5/601 |
| 2001/0039378 A1* | 11/2001 | Lampman | A61B 5/0555 | 600/410 |
| 2002/0156365 A1* | 10/2002 | Tsekos | A61B 5/0555 | 600/411 |
| 2005/0080333 A1* | 4/2005 | Piron | A61B 8/0825 | 600/417 |
| 2005/0228267 A1* | 10/2005 | Bulkes | A61B 6/0414 | 600/415 |
| 2007/0016003 A1* | 1/2007 | Piron | A61B 5/415 | 600/415 |
| 2008/0077005 A1* | 3/2008 | Piron | A61B 5/0555 | 600/411 |
| 2008/0132785 A1* | 6/2008 | Piron | A61B 8/0825 | 600/426 |
| 2008/0255443 A1* | 10/2008 | Piron | A61B 8/0825 | 600/410 |
| 2008/0306377 A1* | 12/2008 | Piron | A61B 8/0825 | 600/422 |
| 2009/0149738 A1* | 6/2009 | Piron | G01R 33/3415 | 600/422 |

* cited by examiner

OPEN ARCHITECTURE TABLETOP PATIENT SUPPORT AND COIL SYSTEM

CROSS-REFERENCE TO RELATED APPLICATIONS

This application is a continuation of and claims the benefit under 35 U.S.C. §120 to application Ser. No. 13/653,062, entitled "OPEN ARCHITECTURE TABLETOP PATIENT SUPPORT AND COIL SYSTEM," filed on Oct. 16, 2012, now U.S. Pat. No. 8,744,550, which is continuation of and claims the benefit under 35 U.S.C. §120 to U.S. application Ser. No. 12/277,061, entitled "OPEN ARCHITECTURE TABLETOP PATIENT SUPPORT AND COIL SYSTEM," filed on Nov. 24, 2008, now U.S. Pat. No. 8,290,569, which claims the benefit of U.S. Provisional Application No. 60/989,898, entitled "Adaptation of Microcontroller for Use In-Bore of an MRI," filed Nov. 23, 2007, and U.S. Provisional Application No. 60/989,904, entitled "Open Architecture Tabletop Coil System," filed Nov. 23, 2007, which are hereby incorporated by reference.

FIELD OF THE INVENTION

The present invention is directed to devices and methods for positioning RF coils adjacent an anatomy of interest for imaging, and for facilitating connections between a magnetic imaging scanner and local RF coils used for the imaging in the bore of the magnetic imaging scanner.

BACKGROUND

In magnetic resonance imaging (MRI), nuclear magnetic resonance (NMR) signals given off by protons in the presence of a strong magnetic field are detected after excitation by a radio frequency (RF) signal using antennae termed "RF coils". Generally speaking, there are two types of RF coils: whole body RF coils, which are used to image large segments of a patient, and "local" or "surface" RF coils, which are configured to image specific anatomies of interest, such as the knees, shoulders, neck, breasts, hands and head.

Whole body RF coils are typically provided with commercially available MRI imaging systems. These RF coils provide a large field of view to accommodate, for example, the chest and abdominal regions of a human subject, and as a result, their fields couple to large amounts of tissue outside the region of interest being imaged. Because of the large field of view, the signal to noise ratio (SNR) of the signal in the anatomy of interest is relatively high, and quality factor of the RF coil is low.

Local RF coils are reduced in size and designed to couple solely with tissue in the region of interest. Local RF coils, therefore, are typically positioned as close as possible to the anatomy of interest, and limit the field of view of an MRI scan to the selected region. The result is a significantly improved SNR and quality factor, and a reduced image size that provides higher resolution of the area of interest.

To provide high resolution images of selected anatomy at high SNR, it is increasingly common to use a number of local RF coils simultaneously in parallel imaging techniques. In these techniques, images are acquired from multiple receive channels, for example 8, 16 or 32 channels receiving signals from 8, 16 or 32 RF coils respectively. In a typical multiple coil array arrangement, for example, several adjacent coils are provided for receiving signals during imaging. Coil switching, multiplexing, or dynamic coil selection strategies are used to optimize a subset of coils for imaging of anatomies of a smaller volume, or to switch between areas of interest during the image acquisition or imaging procedure.

To facilitate these parallel imaging techniques, there is a need for a device that allows an operator to position various types of RF coils adjacent an anatomy of interest while in the bore of a MRI scanner. Such a device should further facilitate connections between the MRI scanner and the RF coils, and allow for circuitry to switch between the coils. The present invention addresses these issues.

SUMMARY OF THE INVENTION

In one aspect, the present invention provides an assembly for magnetic resonance imaging of a patient. The assembly comprises a patient support structure for positioning a local RF coil adjacent an anatomy of interest for imaging, and base removably coupled to the patient support structure for elevating the patient support structure, and a coil connector for receiving the local RF coil. The base is configured for receipt on a table sized and dimensioned for receipt in the bore of the MRI scanner, and the coil connector is coupled to an MR connector configured for connection to the MRI scanner to receive signals from the MRI scanner for controlling local RF coil.

In another aspect, the patient support structure is configured for imaging of the breast, and includes an anterior ramp, a posterior ramp, and a first and a second arched structure extending laterally along the edges of the anterior ramp and the posterior ramp to define an interventional opening therebetween.

In still another aspect, the base comprises a first platform corresponding to the anterior ramp and a second platform corresponding to the posterior ramp. When the patient support structure is aligned on the base, the portion of the ramp between the first platform and the second platform is aligned below and increases the interventional opening.

In another aspect of the invention, at least one of the patient support structure and the base include a plurality of slots and the other of the patient support structure and the base includes a corresponding plurality of tabs, wherein the patient support structure is selectively coupled to the base to minimize the possibility of tipping.

In still another aspect of the invention, the patient support structure includes a receptacle for receiving a tray including the coil connector. The patient support structure can also include an integrated RF coil. The tray can include circuitry for switching between a first RF coil connected to the connector in the tray and a second RF coil integrated in the patient support structure. The tray can also include the tray includes a moveable cover for accessing one or more connectors.

In yet another aspect of the invention, the base includes a raised rim that extends along the edges of the base between the first platform and the second platform. The bottom surface of the base can also include alignment feature for aligning the base with a corresponding alignment feature in a table configured for receipt in an MRI scanner. The alignment feature can, for example, be a tab or a slot.

The foregoing and other aspects of the invention will be described in the detailed description which follows. In the description, reference is made to the accompanying drawings which illustrate a preferred embodiment of the invention.

DETAILED DESCRIPTION OF THE PREFERRED EMBODIMENTS

Figure 1:
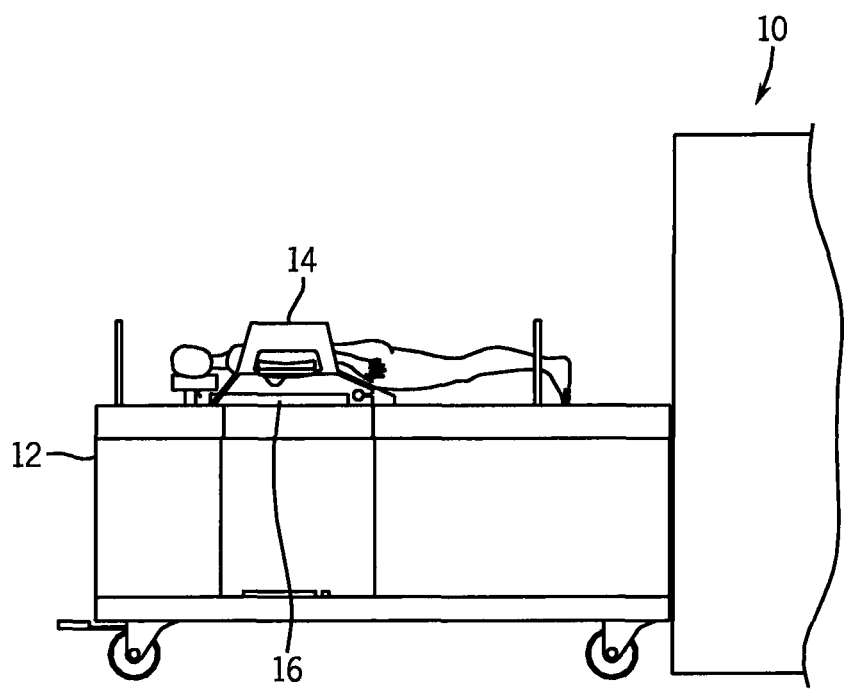
FIG. 1 is a perspective view of a patient supported on a patient support structure constructed in accordance with the present invention.
Figure 5:
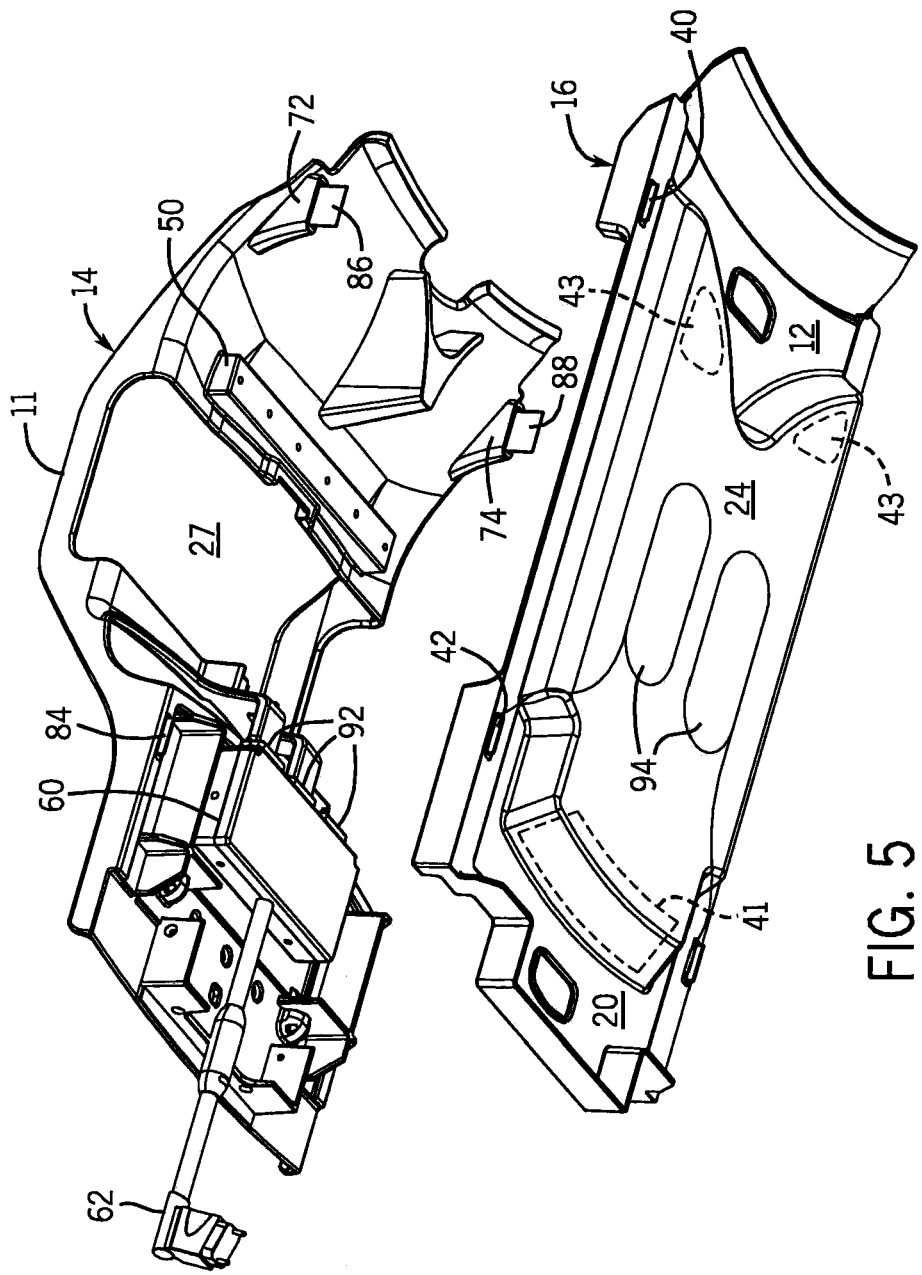
FIG. 5 is a bottom exploded view of the patient support structure 14 and associated base 16.

Referring now to the figures and more particularly to FIG. 1, a patient is shown as supported on a patient support structure 14. The patient support structure 14 is coupled to a base 16, on the MRFs patient table 34 (FIG. 5). The patient can be moved into the bore of the MRI scanner 10 for imaging.

Figure 2:
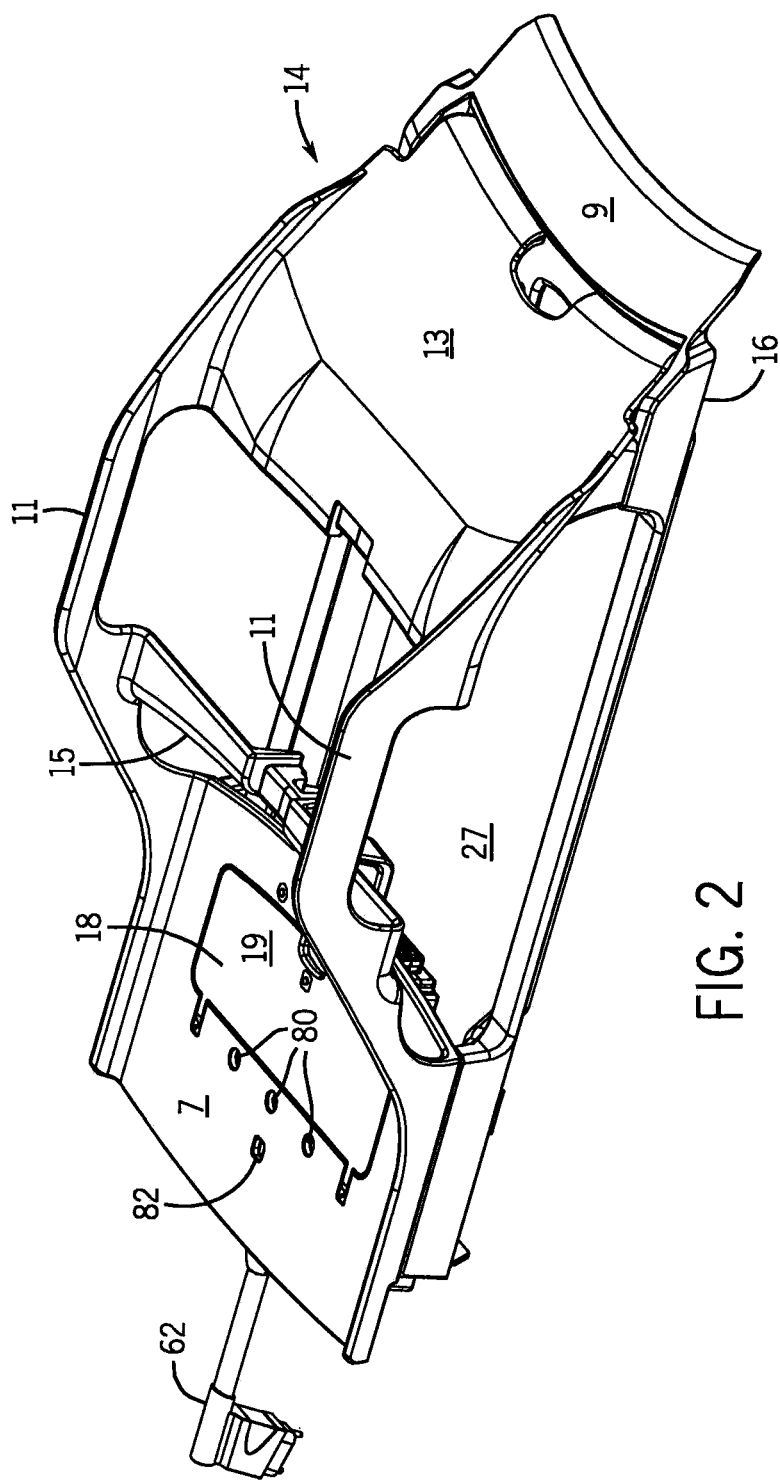
FIG. 2 is a perspective view of the patient support as supported on a base.

Referring still to FIG. 2, the patient support structure 14 is the main structural component for supporting the patient and, as shown here, allows the patient to lie face down with the breasts hanging pendant, while positioned adjacent local RF coils for imaging. Specifically, the patient support structure 14 consists of a head support area or anterior support 9 and a lower support area or posterior support 7, with an interventional opening 27 defined between, and positioned to receive the breasts of the patient. Two arches 11 extend laterally along the opening 27, connecting the head support 9 to the lower patient support 7, providing structure while maximizing the ability of medical personnel to access the breasts of a patient supported on the support member. The arches 11 preferably have a cross section of less than three square inches each. To increase the structural capacity of the patient support, a third cross member 96 (FIG. 4) may be incorporated. The third cross member can be arched or straight and can be, for example, a thin, slender support adjacent to the patient's sternum, or a thin, slender support disposed along the patient's midline (left-right). When a third cross-member is used, it is preferably positioned as far anterior as possible relative to the patient.

Referring still to FIG. 2, the patient support structure 14 further includes a ramp 13 extending upward from the head support 9 and towards the interventional opening 27, and a ramp 15 extending from the opening 27 toward the lower patient support 7. This configuration allow physicians and technicians access to the breast from lateral, medial, superior, inferior and anterior approaches through the interventional opening. The general construction of the patient support structure is 14 described more fully in U.S. Pat. No. 7,379,769, issued on May 27, 2008, which is hereby incorporated by reference for its description of this device. Additional aspects of this invention are also described in the co-pending patent application Ser. No. 12/777,035 entitled "MICROCONTROLLER SYSTEM FOR IDENTIFYING RF COILS IN THE BORE OF A MAGNETIC RESONANCE IMAGING SYSTEM", filed on May 10, 2010, which is hereby incorporated by reference.

Figure 3:
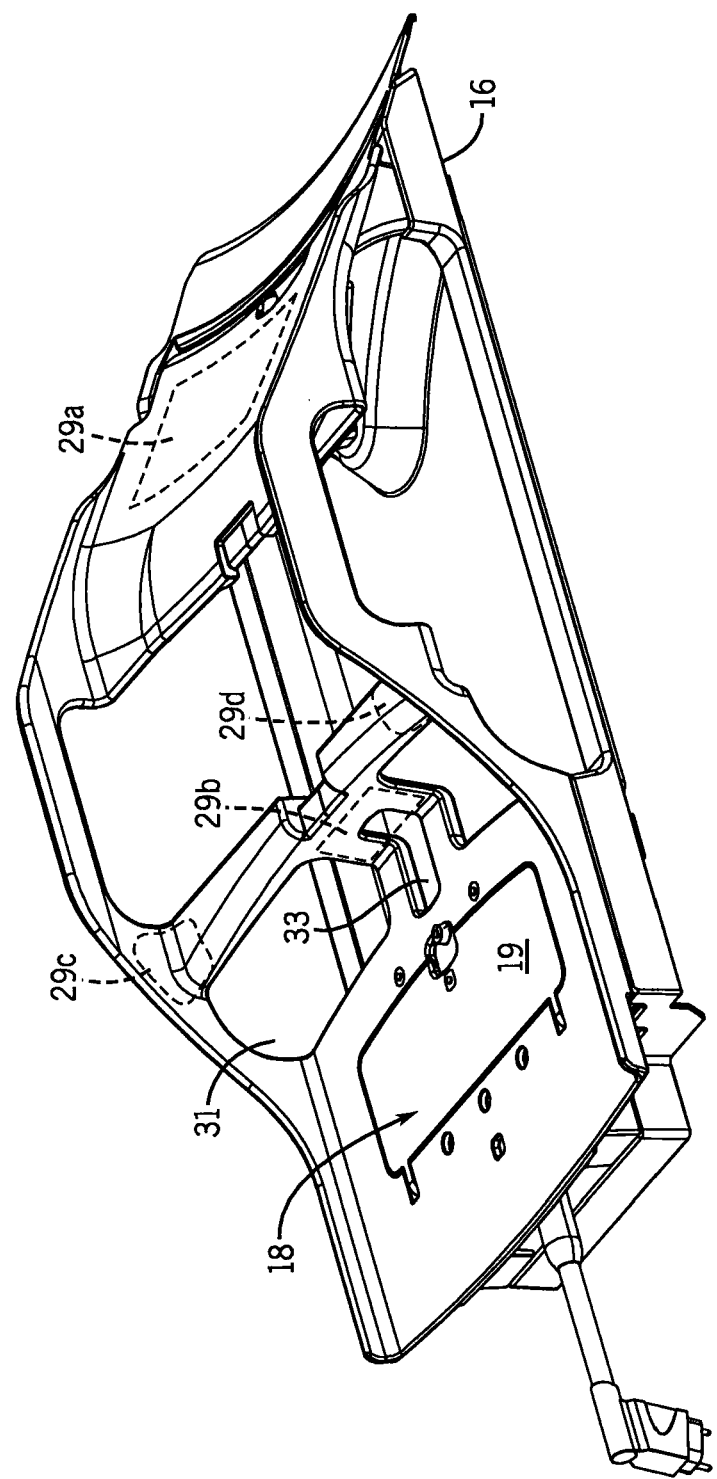
FIG. 3 is an alternate perspective view of the patient support and base configuration.

Referring still to FIG. 2 and now also to FIG. 3. The patient support structure 14 including apertures 31 and 33 for receiving local RF coils at locations selected to provide clinically relevant imaging, particularly to provide lateral imaging of the breast. In addition, RF coils 29a, 29b, 29c, 29d can be integrated into the patient support structure 14 to allow imaging with a higher signal to noise ratio, and in regions outside of the breast. Relevant positions are adjacent to the groin region (29a), neck (29b), underarm (29c, 29d) and adjacent to the back. These RF coils can be either fixed or removable. In addition to the coils shown, other coils, such as chest wall coils for improved imaging of the chest and auxiliary region, and interventional coils for imaging and providing interventional access points can also be used, as well as scout coils for imaging regions associated with breast cancer including: coils located in armpit region for imaging local lymph nodes; coils located in neck region for imaging local lymph nodes; coils located in the groin region; and coils wrapping around the back for coverage of the spine.

Figure 4:
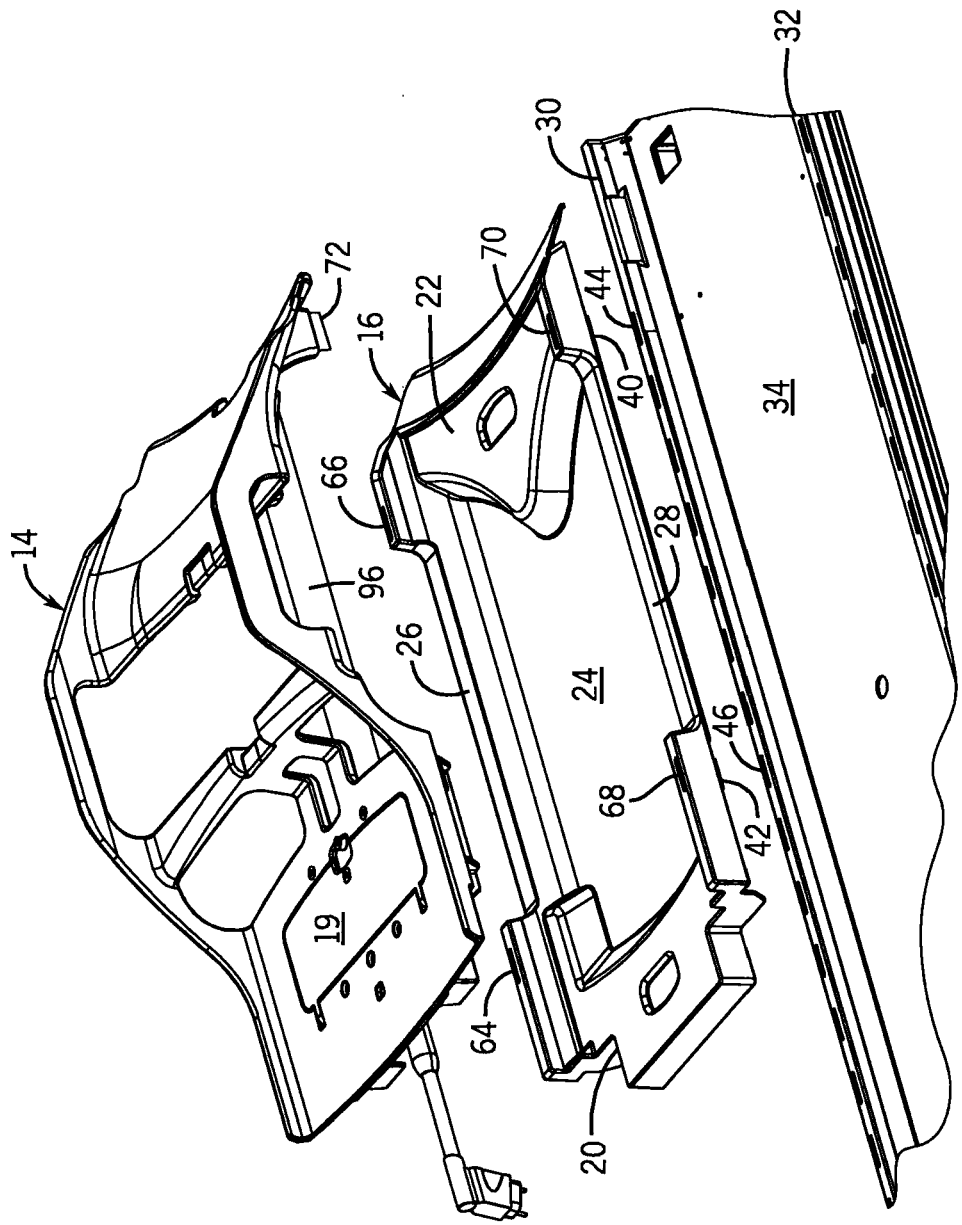
FIG. 4 is an exploded view illustrating the patient support, the base, and an underlying tabletop.

Referring still to FIGS. 2 and 3, and now also to FIG. 4, the base 16 can be a removable structure that can be selectively coupled to the patient support 14 to elevate the patient support 14, and to provide additional support. Referring now specifically to FIG. 4, and also to FIG. 5, in one embodiment, the base structure 16 includes a plurality of slots 64, 66, 68, and 70 that receive mating tabs 84, 86, and 88 formed in a bottom surface at the patient support structure 14 and mechanically link the patient support structure 14 and base 16. The base 16 preferably includes platforms 20 and 22 at the front and back end, and a non-elevated portion 24 connecting the platforms 20 and 22. The elevated platforms 20 and 22 are preferably aligned with the anterior 9 area and posterior 7 portions of the patient support structure and enable additional access to the breast by elevating the patient and patient support 14 (posterior direction) above the underlying tabletop thereby increasing the size of the interventional opening 27 beneath the patient. The non-elevated portion 24 advantageously incorporates a raised rim 26 and 28 for entrapment of blood during biopsy procedures.

The removable base 16 further allows for the use of the same patient support structure 14 with various MRI systems 10. For example, a patient support structure 14 can be selectively positioned on a base 16 that is specifically configured for a particular MRI system 10. The base 16, moreover, can be constructed at a height that is selected for a particular bore diameter of an MRI scanner. For example, the patient support structure 14 could be placed on the MRI table 34 without the base 16 when the MRI scanner has a 60 cm bore, but could be used in combination with the removable base 16 when the MRI scanner has a 70 cm bore, in order to provide better interventional access to the breasts, and to bring the breast tissues closer to the MRI's isocenter for better imaging.

Referring now to FIG. 5, mirrors or prisms 41 and lighting elements 43 to facilitate site lines to the breast for imaging or intervention can be integrated into the base 16. An exemplary position for a mirror 41 is located at the superior line of the breast. Alternatively, the mirror 41 can be configured to be manually adjustable by the user. A low power array of lights can be powered, for example, through a connection to the MRI scanner 10 (not shown). Such lights illuminate the open region of the patient support 14, in order to aid in positioning the patient, coil arrays, and needles. RF coils, such as a loop coil 94 located centrally on each breast, can also be integrated into the base 16. In this application, a connector similar to the connector 17 described above can be provided to allow connection either directly to the MRI scanner 10 or to the cable tray 60, described below. Connectors for connecting RF coils and devices for coupling interventional devices such as compression grids, or needle alignment devices can also be provided in the base 16.

Although the base 16 is shown here as a separate component, the base 16 can also be embodied by legs that retractably extend from a bottom surface of the patient support 14 to raise or lower the patient support 14. The configuration at the base 16 would be done by the operator before the patient is positioned on the patient support 14, particularly to adapt the patient support 14 to the diameter of the bore of the MRI scanner 10 being used, and to create optimal space for the breasts and for physician access to the breasts.

Referring again to FIG. 5, the bottom surface of the base 16 can also include alignment features 40, 42, such as the tabs shown here, to align the base 16 with corresponding apertures 44, 46 in the table 34, and to mechanically couple the base 16 to the table 34 without the need for tools. The alignment features 40 and 42 can be used to guide the base 16 into position on the table 34, and also to position the patient support 14 correctly. Support structures in the base 16 that receive tabs 72, 74 incorporated in the patient support 14 add rigidity to the patient support structure 14 and resist flex. Although a tab and slot connection is shown here, it will be apparent that mechanical fastening devices such as clips, pegs, clamps or straps can be coupled to slots 44 positioned along the edges of the table 34. As shown here, the bottom surface of the patient support surface 14 preferably includes a similar tab structure to allow direct connection of the patient support structure 14 to the table 34.

Referring still to FIG. 2 though 5, both the patient support structure 14 and the base 16 include a number of features which can aid in reducing the tendency of the patient support 14 to tip. Particularly, the base 16 is designed to be weight-bearing, and is configured to be substantially as wide as the top surface of the patient support structure 14 extending as wide as possible in the left-right direction and to use substantially all of the cross-sectional area in the base. Therefore, when a patient is positioned on the patient support structure 14, the patient does not overbalance the edge of the structure. The load, moreover, is supported along the raised edges 30 and 32 of the table 34 corresponding to the MRI system 10. As discussed above, the base 16 includes slots 64, 66, 68, 70 (FIG. 4) for receiving matching tabs 84, 86, 88 (FIG. 5) in the patient support structure 14. In addition to limiting the tendency to tip, these connectors ensure centering of the patient support structure 14 upon entry to the MRI scanner 10. The corresponding slots and tabs, moreover, can provide an electrical connection to power, for example, RF coil elements 94 (FIG. 5) in the base 16.

Referring now to FIGS. 2 and 3, a receptacle 18 is provided in the patient support structure 14 for receiving a cable tray 60, which simplifies connections between the local RF coils and the MRI scanner 10 through the connector 62, as discussed below. Referring now also to FIG. 5, the cable tray 60 is shown received in the cable tray receptacle 18 of the patient support 14. The cable tray 60 provides an electrical connection point for connecting local RF coils to the patient support, and is linked to connector 62 which is configured to be connected to the control system of the MRI scanner 10 for driving the RF coils. To limit noise, coaxial cables and signal lines are routed through the cable tray 60 and to the MRI system 10. Local RF coils that are coupled to the patient support structure 14 or to the base 16 can be routed or connected to the cable tray 60 states indicator lights 80a, 80b, 80c, can be provided to indicate that the RF coils connected to the cable tray 60 are a valid coil combination. An indicator 82 is activated by circuitry in the cable tray 60 when the connector 62 is fully connected to the MRI scanner 10.

The housing of the cable tray may, as shown, enclose the connection points, and the electrical connections made by opening or removing a panel or panels 19 in the anterior end 9 of the patient support 14, so that RF coils can be connected to receptacles in the cable tray 60. In order to facilitate access to the connections of the cable tray 60 by the user, and to limit access by the patient, the panel 19 can be a folding, sliding or like covering that is integrated into the housing. Alternatively, the housing of the cable tray 60 can directly incorporate connectors (plugs or receptacles) which permit electrically connecting detachable RF coil arrays directly to the housing at cable tray 60. The cable tray 60 is removably attached to the patient support 14 in receptacle 18 to allow a user to interchange the cable tray 60 for a system upgrade, transfer between magnets, or other reasons. Suitable connectors include, for example, latches, sliders, hook and loop fasteners, threaded fasteners, quarter-turn fasteners, and other mechanical coupling devices.

Internally, the cable tray 60 can include RF circuits for signal filtering, signal combination, shield current traps and baluns. Circuitry for determining the appropriate combination of RF coils can also be provided, and may include, for example, a microprocessor, or multiplexing or switching circuitry that provides intelligent selection of the RF coil arrays for imaging. Visual indicators such as light emitting diodes can be located in the cable tray 60 to provide coil status and configuration indicators to the user.

Although shown on a specific end of the patient support 14, the cable tray 60 can be mounted at the anterior support 9 or posterior support 7 thereby allowing the cable tray 60 to be adapted to different MRI devices or scanners 10. The cable tray 60 can be, as shown in the figures, centered between the left and right sides of the patient support 14, and is preferably removable for cleaning. The cables are preferably sized to be sufficiently long to allow left/right and anterior/posterior movement of an attached RF coil for breast imaging, and to take up slack and tension, but are restricted in length to prevent tangling or interference with the moving parts of the system, or interference with relative motion between the patient support structure 14 and the bore of the MRI scanner 10.

The cable tray 60 can include a plurality of plugs or receptacles corresponding to cables attached to RF coil arrays and elements that are moveable in the system. Cables can be permanently attached to the RF coil, or can include a connector that mates with the coil element. Alternatively, cables can be permanently attached to the cable tray, and include connectors for receiving mating connectors associated with local RF coils and coil elements. The RF coils can, for example, be provided with cords of 20-60 cm length which permit free positioning without undue signal loss or the possibility of looping.

Referring now to FIG. 5, a slider 50 coupled to the patient support structure 14 provides an attachment point for compression devices and RF coils. The sliders 50 are rigidly attached to the patient support structure 14, and may be attached to the patient support structure 14 on the posterior 9, anterior 7, or both sides of the interventional gap 27 simultaneously. Compression plates and compression plates housing RF coils can be coupled to the slider 50 with several degrees of freedom and can, for example, house coils specifically designed for improved imaging of the chest wall. The RF coils in the compression system can be coupled to the MRI system 10 through the cable tray 60, as described above. Compression plates and other devices suitable for the application are described more fully in U.S. Pat. No. 7,379,769, issued on May 17, 2008, which is hereby incorporated by reference for its description of these devices.

In use, therefore, the present invention provides many advantages over the prior art, providing significantly improved access to breast tissue for imaging and intervention, particularly from beneath the breast, superior and inferior to the breast. For newer MRI types having geometries with large bore sizes (for instance 70 cm versus 60 cm in diameter), the benefit of the larger bore can be utilized for breast imaging by raising the patient support structure 14 to a higher position in the bore for greater access. Additionally, by removing the base 16, the patient support structure 14 can be lowered to provide room for larger patients. The base 16, for example, can ensure access for the larger magnet (i.e. 70 cm bore), while the patient support structure 14 can be used without a base 16 for a smaller magnet (i.e. 60 cm bore), while the patient is located near the same relative central point in the magnet.

Integrated coils at openings located at the groin region can accommodate coils allowing for survey scans of that region for signs of cancer progression. RF coils may also be provided at the neck region, allowing scanning of the lymph nodes and spine in that region. RF coils may also be attached at the back region to allow for scanning of the spine while the patient is positioned prone for breast imaging. Through the use of RF coil switching technology (i.e. the ability to sample from various combinations of coils in a dynamically switching fashion), these coil arrays can be selectively activated or deactivated during specific scanning protocols or dynamically through a protocol, i.e. scan the breast region, then selectively scan the axilla then scan the back, etc.

An important feature of the disclosed invention is the ability to incorporate multiple coils to provide coverage for a selected anatomy, or regions of interest. These coils can be integrated into the frame of the tabletop, the base structure, or fixably attached to the tabletop by way of compression plates or support structures. The invention also importantly provides structure for restraining a patient in an appropriate position for imaging throughout a procedure. The patient support structure 14 described above, for example, has been shown to be sufficiently strong to support a patient of between three hundred and fifty and five hundred pounds with a safety factor of four, even without additional supports or structures.

A preferred embodiment of the invention has been described in considerable detail. Many modifications and variations to the preferred embodiment described will be apparent to a person of ordinary skill in the art. For example, although the invention is described here specifically for use in breast imaging, it will be apparent to those of skill in the art that many of the novel features described can be embodied in structures configured for other anatomies of interest. Although tab and slot connections have been described above in a number of applications, it will be apparent that the slots and tabs can be received and that other types of mechanical connections can also be used. Furthermore, although the cable tray 60 and receptacle 18 are shown at a specific end of the patient support structure 14, it will be apparent to those of ordinary skill in the art that this orientation could be received. Therefore, the invention should not be limited to the embodiment described. To apprise the public of the scope of this invention, the following claims are made:

The invention claimed is:

1. An assembly for magnetic resonance imaging (MRI) of a patient, the assembly comprising:
a plurality of local RF coils, wherein the local RF coils are configured to be positioned adjacent to an anatomy of interest;
a patient support structure configured to support of the patient;
a base removably coupled to the patient support structure, the base being configured for receipt in the bore of an MRI scanner; and
an interface configured to connect the plurality of local RF coils and the MRI scanner and to selectively control a first local RF coil and a second local RF coil included in the plurality of local RF coils.

2. The assembly as recited in claim 1, wherein the interface further comprises a coil connector, the coil connector being coupled to an MR connector configured for connection to the MRI scanner to provide signals from the MRI scanner to the plurality of local RF coils.

3. The assembly as recited in claim 2, wherein the interface includes a cable tray connected to the coil connector and configured to be received in the patient support structure via a receptacle.

4. The assembly as recited in claim 3, wherein the cable tray provides an electrical connection to the plurality of local RF coils and the coil connector.

5. The assembly as recited in claim 1, wherein at least one of the plurality of local RF coils is integrated into the patient support structure.

6. The assembly as recited in claim 1, wherein at least one of the plurality of local RF coils is integrated into the base.

7. The assembly as recited in claim 1, wherein the interface is further configured to connect combinations of the plurality of local RF coils.

8. The assembly as recited in claim 1, wherein the interface is further configured to determine the combinations of plurality of local RF coils to selectively control.

9. The assembly as recited in claim 8, further comprising indicator lights configured to indicate whether the combination of the plurality of local RF coils connected to the interface are valid combinations.

10. The assembly as recited in claim 1, wherein the plurality of local RF coils are removable.

11. The assembly as recited in claim 1, wherein the patient support structure is configured for imaging of the breast, and includes an anterior ramp, a posterior ramp, and a first and a second arched structure extending laterally along the edges of the anterior ramp and the posterior ramp to define an interventional opening therebetween.

12. The assembly as recited in claim 11, wherein the base comprises a first platform corresponding to the anterior ramp and a second platform corresponding to the posterior ramp, wherein when the patient support structure is aligned on the base, wherein the portion of the ramp between the first platform and the second platform is aligned below and increases the interventional opening.

13. The assembly as recited in claim 1, wherein at least one of the patient support structure and the base include a plurality of slots and the other of the patient support structure and the base includes a corresponding plurality of tabs, wherein the patient support structure is selectively coupled to the base.

14. The assembly as recited in claim 1, wherein the base comprises one or more legs removably coupled to a bottom surface of the patient support structure to raise the patient support structure.

15. The assembly as recited in claim 1, wherein a bottom surface of the base comprises an alignment feature for aligning the base with a corresponding alignment feature in a table configured for receipt in an MRI scanner.

16. The assembly as recited in claim 15, wherein at least one of the alignment feature and the corresponding alignment feature comprises a tab and the other of the alignment feature and the corresponding alignment feature comprises a slot.

17. The assembly as recited in claim 16, wherein the slot and tab include electrical connectors for electrically connecting the patient support structure to the base.

18. The assembly as recited in claim 1, wherein the patient support structure comprises an integrated RF coil for imaging at least one of a groin region, a neck, an underarm and a back of the patient.

19. A method of magnetic resonance imaging (MRI) of a patient using different types of MRI scanners, the method comprises:
   providing a patient support structure configured to support of the patient;
   removably coupling a base to the patient support structure, the base being configured for receipt in the bore of a first type of MRI scanner having a first bore size;
   decoupling and removing the base from the patient support structure;
   placing the patient support structure on a table of a second type of MRI scanner having a second bore size; and
   positioning a local RF coil adjacent an anatomy of interest for imaging using the second type of MRI scanner.

20. The method as recited in claim 19, further comprising selectively controlling a first local RF coil and a second local RF coil included in the plurality of local RF coils.

\* \* \* \* \*